United States Patent [19]

Meshel

[11] Patent Number: 5,191,897
[45] Date of Patent: Mar. 9, 1993

[54] SELF-ADHERENT EYE OCCLUDER

[75] Inventor: LeRoy G. Meshel, San Francisco, Calif.

[73] Assignee: Lens Plus Corporation, San Francisco, Calif.

[21] Appl. No.: 725,788

[22] Filed: Jul. 8, 1991

Related U.S. Application Data

[63] Continuation of Ser. No. 349,459, May 8, 1989, abandoned.

[51] Int. Cl.$^5$ .................................................. A61F 9/00
[52] U.S. Cl. .......................................... 128/745; 2/15; 128/858
[58] Field of Search ................... 128/745, 858, 888; 604/294, 301, 302; 2/15, 440, 441

[56] References Cited

U.S. PATENT DOCUMENTS

| | | | |
|---|---|---|---|
| 2,172,573 | 9/1939 | Blumenthal | 2/15 |
| 4,599,746 | 7/1986 | Stoner | 2/15 |
| 4,682,371 | 7/1987 | Heltman | 2/15 |
| 4,862,902 | 9/1989 | Goffman | 128/858 |
| 4,944,040 | 7/1990 | Riedel et al. | 2/15 |

Primary Examiner—Peter A. Aschenbrenner
Attorney, Agent, or Firm—Flehr, Hohbach, Test, Albritton & Herbert

[57] ABSTRACT

In accordance with the present invention, a self-adherent eye occluder for use in visual diagnostic testing and treatment is provided which includes an eye occluder that is designed to drape or contour over the eye and substantially block its vision. The eye occluder need not be fully light occlusive when it is placed over the eye, as it is intended for use in visual function and neuropthalmologic testing and treatment in which it is unnecessary to block light. The eye occluder is further provided with a pressure-sensitive adhesive material applied to at least a portion of a posterior side of the eye occluder sufficient to adhere the eye occluder to either the periorbital tissue about the eye or to spectacles worn over the eye. The occluder can be constructed to be disposable. The present invention also includes a method for using the eye occluder to occlude an eye, while simultaneously allowing the patient, visual tester, or other practitioner to transcribe information or records directly on an anterior surface of the occluder for efficient record-keeping and treatment.

13 Claims, 2 Drawing Sheets

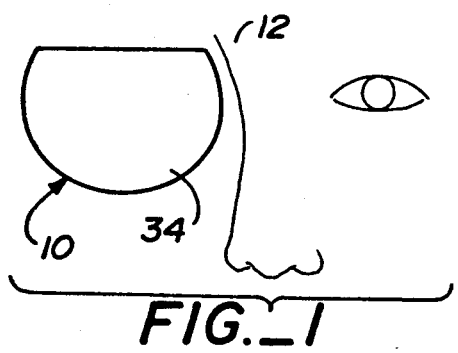
FIG._1    FIG._1A
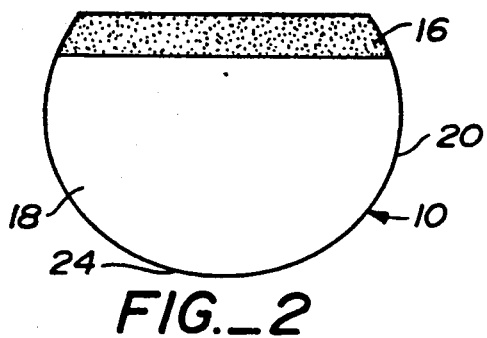 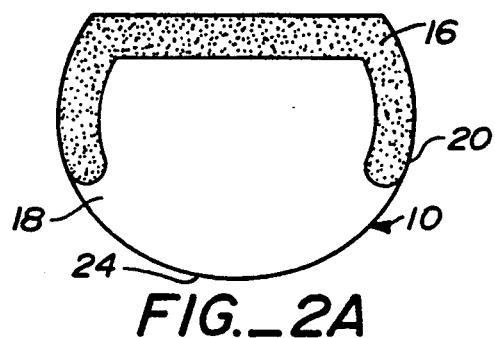
FIG._2    FIG._2A
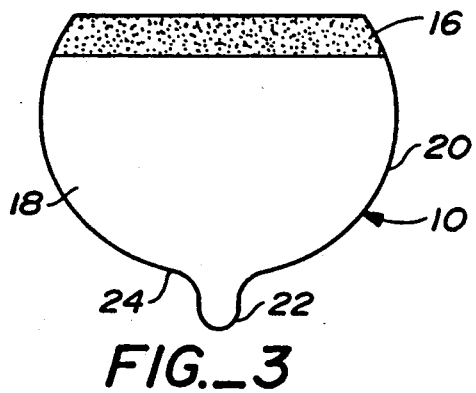 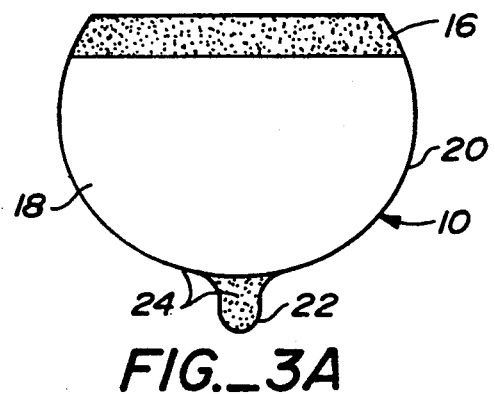
FIG._3    FIG._3A
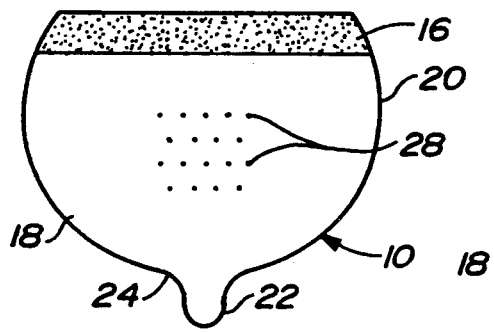 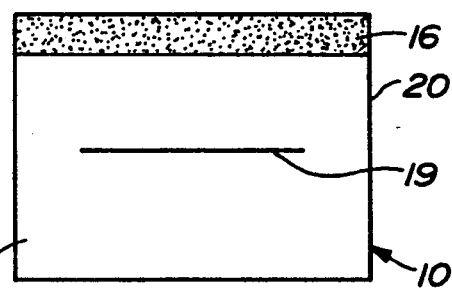
FIG._4    FIG._5

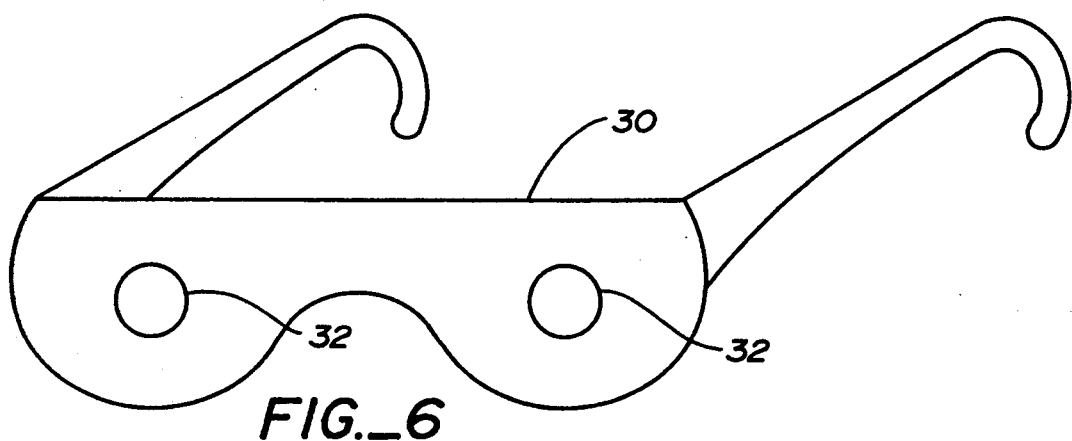
FIG._6
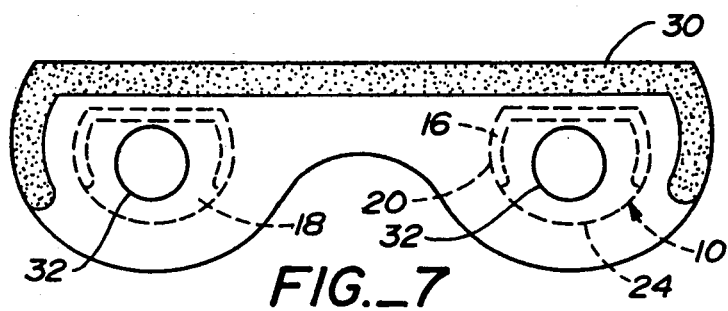
FIG._7
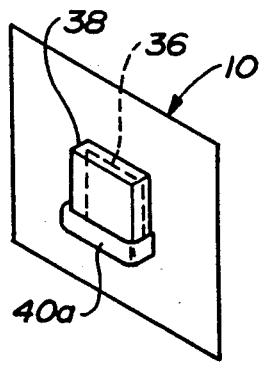
FIG._8
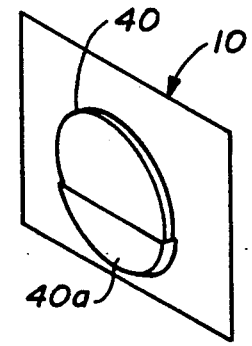
FIG._8A
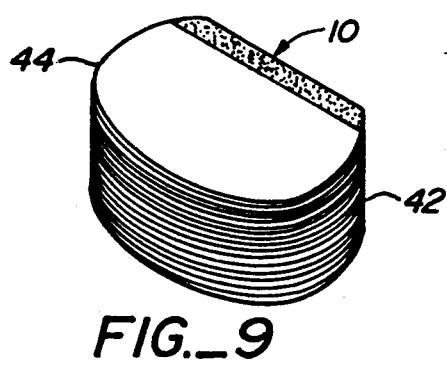
FIG._9

SELF-ADHERENT EYE OCCLUDER

This is a continuation of application Ser. No. 07/349,459 filed May 8, 1989, now abandoned.

FIELD OF THE INVENTION

The present invention relates to eye occluders for visual function testing and diagnosis, and treatment of eye diseases, and to a method for occluding the eye. More particularly, the present invention relates to transient use, self-adherent eye occluders which are fast to apply and remove, and a method of using the same, in which the eye occluder has a pressure-sensitive adhesive material applied to at least a portion of the posterior surface of the occluder, and has suitable characteristics to adhere it to either the periorbital tissue about the eye or directly to spectacles worn over the eye. The eye occluder further can be constructed to be disposable.

BACKGROUND OF THE INVENTION

In the eye care field, there are generally two types of devices currently used by eye care practitioners for occlusion of the eye. One such device is designed for transient use and is placed in front of the eye to block or modify its vision, enabling the vision tester to determine visual function of the unoccluded eye or interrelation of function between eyes. Transient occluders for ocular diagnostics are typically non-disposable and occlude or modify the vision in one eye. These occluders are usually hand-held and made of hard plastic, metal, or glass in the shape of a paddle, mask, or clip-on device. A non-disposable transient occluder of a smaller rounded shape is also used in trial spectacle frames or can be incorporated into a machine called a phoropter, used to determine a patient's refractive error for spectacle or contact lens prescriptions or to perform other optical or neuropthalmalogic testing.

Non-disposable transient occluders are problematic for several reasons. First, it is often difficult for the patient or practitioner to place the occluder in the correct position over the patient's eye for accurate vision testing. It is especially difficult for a practitioner to adequately occlude an infant's eye using a non-disposable transient occluder. Younger and elderly patients often lack the muscular coordination or patience to hold the occluder steadily in place. It is difficult for these patients to keep the hand-held occluder in proper position over the eye while undergoing vision testing. Elderly patients often have advanced arthritis, poor coordination, neurological tremors, or physical abnormalities of the head or neck causing them to have extreme difficulty in keeping the hand-held occluder properly positioned over the eye, and at the same time, sit behind the phoropter in proper position. Non-experienced vision testing agents, such as school visual screeners, non-medical practioners in mass screening projects or inexperienced eye technicians collect spurious vision testing data because of improperly placed non-disposable occluders.

In addition, use of trial frame occluders is time consuming and difficult when the practitioner wishes to quickly determine visual accuity. These problems lead to inaccurate visual function testing. This problem is compounded when the testing is done for longer time periods because the patient and practitioner become fatigued.

Non-disposable transient use occluders are made of a permanent hard material, such as plastic, metal, or glass. These recurrently-used occluders can transmit bacteria or viruses from patient to patient since they are reused. For example, diseases such as viral epidemic keratoconjunctivitis can be easily transmitted from patient to patient by reusing the non-disposable transient occluders, since they come in contact with the face and hands of successive patients. It has also been suggested that the human HIV virus, implicated in AIDS and ARC syndrome, can also be transmitted via bodily secretions, such as tears. The use of disposable transient occluders obviates this problem.

Another disadvantage of non-disposable transient occluders constructed of hard materials is their potential for scratching the delicate plastic lenses of spectacles or coated lenses.

Transient use occluders often distort vision by changing the effective optical power of spectacles, when pressure is placed on the spectacles by the occluder, thereby altering the position of the spectacles relative to the patient's eye. This distortion interferes with accurate visual testing and diagnosis, especially in patients whose vision is highly myopic, hyperopic, or astigmatic, or in patients who are aphakic, i.e., those who have had cataract extraction.

A second type of occluder designed for extended periods of wear, typically 2-48 hours, is used solely for treatment of vision abnormalities, not for diagnostic testing. These occluders are typically used in the treatment of strabismus (eye turn), amblyopia (lazy eye), and diplopia (double vision). This extended-wear occluder comes in the form of a complexly constructed eyepatch made of layered fabric, paper, or plastic, such as those disclosed in U.S. Pat. Nos. 4,793,003 and 3,068,863. These extended-wear occluders have a surrounding area of adhesive material, for placement on the periorbital tissue about the eye for relatively long periods of time and are typically disposable and replaced periodically. Their function is to keep the eye visually occluded and devoid of significant amounts of ambient light.

These extended-wear disposable occluders are constructed to adhere to the patient's periorbital tissue for hours to days at a time. These occluders are not designed for fast application, fast removal, disposable, transient use in that they are necessarily firmly attached to the face and adherent to the periorbital tissue for the full circumference of the patch. This makes their fast application and fast removal for disposable transient use inefficient and therefore infeasible. The extended-wear occluders are not designed for attachment directly to spectacles for vision testing. Moreover, they are too complex in design and construction and therefore, too expensive for fast application, fast removal, disposable, transient use. The extended-wear occluders must necessarily contain a type of adhesive, which often leaves a sticky residue on the skin after removal.

The extended-wear occluders are often designed so that a strip of adhesive maintains the eye beneath the occluder in a closed position. This requires careful application of the occluder so that the cornea (front surface of the eye) is not abraded by the overlying adhesive or occluder. In addition, these occluders are difficult to properly place. Because of their firm, prolonged, total adhesive occlusion of the eyes, the extended-wear occluders often cause allergic reactions to the patient's skin surrounding the eye, and sweating, irritative reactions due to prolonged wear of the occluder.

The primary objective of extended-wear occluders is to block as much vision and prevent as much light as possible from contacting the eye. Vision and light occlusive therapy are used to immobilize the non-affected eye while the uncovered affected eye is free to move in response to visual stimuli. It is believed that even small amounts of light passing through the extended-wear eye occluder to the amblyopic eye stimulates undesirable eye movement, thereby decreasing the efficacy of treatment. It is also believed that scleral transmission of light in the non-amblyopic eye aids in maintaining abnormal neuroconnections in the amblyopic eye, promoting and maintaining the amblyopic condition. Therefore, light occlusion is thought to be important for efficient treatment of this visual deficit.

Thus, extended-wear occluders are used to treat eye problems that require a substantially complete occlusion of vision and light. Examples of these extended-wear disposable occluders are disclosed in U.S. Pat. No. 4,793,003 to Riedel. Riedel discloses a light-occlusive, extended-wear, self-adherent eye occluder comprising an absorbent pad with a non-adherent lower surface, a thin microporous polymeric film overlying the upper surface of the pad, pressure-sensitive adhesive means to adhere the patch to the eye socket and a removable protective liner covering the non-adherent lower surface of the absorbent pad and the exposed portion of the pressure-sensitive adhesive. One of the primary features of the eye occluder disclosed in Riedel is that the polymeric film is capable of blocking at least 95% of the light from a preselect wavelength impinging on the film. By virtue of its intended function, the design and construction of this occluder is complex and relatively expensive to produce. Therefore, it is inadequate in its design and has economic constraints for transient, one-time use.

Another extended-wear, light-occlusive extended-wear product known as Opticlude® Orthoptic Eye Patch sold by 3M, comprises an absorbent pad having non-adherent films on its upper and lower surfaces. The patch is secured to the eye socket by use of a medical tape, and a removable liner protects the pad and adhesive layer prior to use. The Opticlude patch is said to effectively block about 75% of the incoming ambient light.

Another light-occlusive patch is sold in Europe by Beiersdorf and is known as Elastopad-lite occlusive plaster. This product is a laminate comprising an absorbent pad, a layer of black non-woven material and a layer of porous polyvinyl chloride overlying the black non-woven layer. A piece of tape overlies the polyvinyl chloride layer and extends beyond the periphery of the other layers of the patch to adhere the patch to the eye socket. The Elastopad product is stated to block virtually all of the ambient light. However, it is uncomfortable in that it is thick and relatively nonconformable.

Other extended-wear devices are used to protect the eye from contact with objects or light after surgery or after a wound to the eye. For example, U.S. Pat. No. 3,068,863 to Bowman discloses a protective eye device which includes a protective patch having a convex outer edge extending downwardly and inwardly from the upper edge, a lower convex edge of shorter radius than the upper edge and the outer edge, and an inner concave edge extending from the lower edge to the other end of the upper edge to form a tab portion. The protective device of Bowman also discloses an adhesive layer on one side of the patch and a protective strip disposed on the adhesive layer intermediate the edges of the patch. The adhesive layer overlies the eyelid and holds it in closed position thereby preventing access of light to the eye.

U.S. Pat. No. 4,709,695 to Kohn discloses a protective device for the eye which includes an adhesive base that attaches to the patient's skin and surrounds the area to be protected. A protective covering is coupled to the base by adhesive or Velcro. The covering can be repeatedly decoupled and recoupled with the adhesive base without detaching the base from the patient's skin. The device thereby provides repeated access to the protected area without damaging the skin.

Accordingly, there exists a need for easy to apply and easy to remove, self-adherent, transient-use eye occluders for use in everyday visual function testing and treatment. There also exists a need for an easy to apply, easy to remove, transient occluder which is economical to manufacture so as to be disposable. A need also exists for a self-adherent transient eye occluder which is easy to position and remove, leaving minimal residual debris on the wearer's face or spectacles.

The eye occluder of the present invention is a self-adhering occluder which is designed to substantially block vision, yet not necessarily be light occlusive. It is primarily intended for use in performing short-term visual and neuroopthalmalogic diagnostic testing and treatment.

Accordingly, one object of the present invention is to provide a disposable, self-adherent, easy to apply and easy to remove, eye occluder which substantially blocks vision when placed over an eye and is used in performing visual function diagnostic testing and treatment, which does not require lid or eye immobilization and full eye occlusion.

A further object of the present invention is to provide a self-adherent eye occluder that can be disposed of after each use and does not transmit bacteria or viruses from patient, since it is not reused.

Another object of the present invention is to provide a self-adherent eye occluder which is easily placed by the patient or physician in proper position over the eye or directly on the spectacles, and which is easily removed, leaving no significant residual debris on the skin or spectacles.

A further object of the present invention is to provide a self-adherent eye occluder which does not change the effective optical power of spectacles when the occluder is placed directly on the spectacles of the wearer, and does not damage the optical qualities of the spectacles, once the occluder is removed.

Another object of the present invention is to provide a disposable eye occluder which does not cause allergic reactions to the eyes or skin of the wearer.

A further object of the present invention is to provide a disposable self-adherent eye occluder which is non-irritating and contains an adhesive which does not scratch or irritate the wearer's skin or spectacle lenses, when the eye occluder is placed thereon.

Another object of the present invention is to provide a self-adherent eye occluder for visual testing which does not need to be held in place by the patient, technician or other testing agent, or treating physician.

A further object of the present invention is to provide a self-adherent eye occluder for testing of patients' visual field and eye-muscle coordination.

Another object of the present invention is to provide a self-adherent eye occluder for visual testing negating refractive error, using pinhole and thin slit openings on the occlusive shield.

Another object of the present invention is to provide a self-adherent eye-occluder which supports refractive and diagnostic lenses.

SUMMARY OF THE INVENTION

In accordance with the present invention, a self-adherent, transient-use eye occluder for use in visual diagnostic testing and treatment is provided which can include an eye occluder that is designed to drape or contour over the eye and substantially block or modify its vision. The eye occluder need not be fully light occlusive when it is placed over the eye, as it is intended for use in visual function testing and treatment in which it is unnecessary to block light. The eye occluder can further be provided with a pressure-sensitive adhesive material applied to at least a portion of the posterior side of the eye occluder sufficient to adhere it to either the periorbital tissue about the eye or to spectacles worn over the eye. The occluder can be constructed to be disposable.

In another embodiment, the present invention can also include a self-adherent, transient-use, eye occluder for use in visual diagnostic testing and treatment which is disposable and semi-opaque or opaque. The eye occluder can be constructed to drape or contour over an eye and to have an opening for accepting trial lenses, prism lenses, or other diagnostic lenses, such as a Maddox rod, red lens, or green lens. The eye occluder can further include a pressure-sensitive adhesive material applied to a at least a portion of its posterior surface sufficient to adhere the eye occluder either to the periorbital tissue about the eye or to spectacles worn over the eye.

Another aspect of the present invention comprises a portable eye occluder assembly for use in visual diagnostic testing and treatment which includes a plurality of disposable eye occluders that are designed to drape or contour over the eye and substantially block vision of the eye without being fully light occlusive when covering the eye. Each of the eye occluders in the assembly can include a pressure-sensitive adhesive material applied to at least a portion of the posterior side of each eye occluder, sufficient to adhere the eye occluder to either the periorbital tissue about the eye or to spectacles worn over the eye. The assembly can be further constructed so that the eye occluders are stacked successively on each other and are removably bound to each other in a pad-like assembly by the adhesive which is applied to each eye occluder, so that when pressure is applied to an anterior side of one eye occluder, the adhesive removably fastens that eye occluder to an anterior side of a second eye occluder, and successive eye occluders are fastened in the assembly to each other, in this manner. The assembly allows portability for the user. The user can remove a single eye occluder at a time from the assembly as needed for use in covering a patient's eye, while allowing the remaining eye occluders to be bound in the pad-like assembly.

The eye occluder of the present invention can be constructed of any reasonably flexible, soft material that can be draped over the eye and secured to periorbital tissues. Alternatively, the occluder of the present invention can be constructed of a more rigid material, such as plastic, which can be draped over the eye to form a cup-shaped occluder that will cover the eye without irritating the eyelashes or lids, and will not scratch spectacles if the occluder is placed directly on the lens. Suitable materials for construction of the eye occluder can include, but are not limited to, any economically feasible material such as paper, plastic, cardboard or cloth.

The adhesive material can be applied to a portion of the posterior side of the eye occluder of the present invention, preferably a portion of the peripheral edges of the occluder. The adhesive can be pressure-sensitive, so that light pressure exerted by the hands against the anterior side of the eye occluder will adhere it to the skin or directly to the spectacles. The adhesive can be applied to the upper peripheral edge of the eye occluder only, or to the side or bottom peripheral edges of the eye occluder, or to all of its edges. The only requirement is that adhesive material be applied to a sufficient portion of the posterior side of the eye occluder, to adhere it to the periorbital tissue surrounding the eye or to spectacles worn over the eye. Different embodiments of the adhesive placement can be used, depending on the reason for use of the eye occluder. For example, in visual testing with a patient sitting upright in the examining chair, it may be desirable to have the adhesive applied to an upper edge only leaving the lower edge free and unsecured.

The adhesive preferably has low tack characteristics so that when the eye occluder is removed it does not leave any significant residual debris on the skin or spectacles. The adhesive is preferably biocompatible with the wearer's skin and hypo-allergenic to both the eyes and skin. Preferably, the adhesive material should have high shear characteristics, so that the occluder will hold firmly against gravity to the patient's periorbital tissue or spectacles.

Moreover, the adhesive in all of its embodiments, can have a backing applied to the adhesive surface, so that the posterior surface of the occluder is not tacky and adherent until the backing is peeled away when the practitioner is ready to use the occluder. The backing has a dual function in that it can be peeled away from the adhesive material between about ⅓ to ½ of its longitudinal length and folded over to rest on the cheekbone of the subject. This folded over portion of the backing serves to keep the occluder away from the eyelid and eyelashes.

The eye occluder as described herein can have a number of alternative embodiments. In one embodiment, the eye occluder can be constructed as a oval or square-shaped patch. In another embodiment, the occluder can be constructed with a tab at its lower surface to facilitate handling and placement of the eye occluder over the eye or on the spectacles.

In another embodiment, the eye occluder can be constructed so that it is perforated with a plurality of pinholes or has a thin slit opening at an approximate center of the eye occluder for visual testing. These embodiments are useful in determining a patient's best possible visual accuity without performing a refractive examination or eliminating the patient's astigmatic error.

A further embodiment can include the eye occluder of the present invention removably fastened by the adhesive material to a mask-type apparatus in which the mask apparatus has openings in front of each eye. The eye occluder of the present invention can be adhered to the mask over one or both openings by application of pressure on the anterior side of the eye occluder, thereby enabling the pressure-sensitive adhesive material to adhere the eye occluder to the mask. Alternatively, the occluder can be adhered to the mask, for example, by the use of Velcro ®. The mask can be a permanent apparatus, for example, in the form of an eyeglass frame constructed of plastic, or it can be constructed of disposable material such as cardboard on plastic.

A further embodiment of the present invention can include a disposable semi-opaque or opaque eye occluder designed to drape or contour over an eye. The eye occluder can have an opening for accepting trial lenses, prism lenses, or other diagnostic lenses, such as Maddox rods and red lenses or green lenses. Maddox rods, and red lenses are useful in diagnosing extraocular muscle problems or neuroophthalmalogic problems. In this embodiment, the occluder can have support means for holding the diagnostic lens in place in the occluder. The support means can include an envelope-like fold of material into which the bottom edge of the lens can be inserted. The occluder can further include pressure-sensitive adhesive material applied to at least a portion of the posterior side of the occluder about the eye sufficient to adhere it to either the periorbital tissue of the eye or to spectacles worn over the eye.

Another aspect of the present invention includes a method for occluding an eye for visual function testing and treatment comprising placing a self-adherent, transient-use eye occluder on periorbital tissue or spectacles, wherein the eye occluder is constructed to drape or contour over an eye without being fully light occlusive. The eye occluder can further include a pressure-sensitive adhesive material applied to at least a portion of a posterior side of the eye occluder sufficient to adhere it to either the periorbital tissue or to the spectacles. This method allows a patient, visual tester, or other practitioner to conveniently record or convey information or records, by transcribing such information directly on an anterior surface of the occluder.

BRIEF DESCRIPTION OF THE DRAWINGS

FIG. 1 is a schematic diagram of a subject wearing the eye occluder of the present invention constructed to drape or contour over the eye.

FIG. 1A is a schematic diagram of a patient wearing the eye occluder of the present invention directly on the spectacles.

FIGS. 2 and 2A are a rear plan view of the eye occluder of the present invention, showing the posterior surface of the eye occluder, and alternative embodiments of adhesive placement represented by cross-hatched lines.

FIGS. 3 and 3A are a rear plan view of the posterior side of the eye occluder of the present invention showing an alternative embodiment.

FIG. 4 is a rear plan view of the posterior side of the eye occluder of the present invention, showing still another embodiment of the invention.

FIG. 5 is a rear plan view of the posterior side of the eye occluder of the present invention, showing another embodiment of the invention.

FIG. 6 is a front elevation view showing another embodiment of the eye occluder of the present invention.

FIG. 7 is a rear plan view of the eye occluder embodiment of FIG. 6.

FIG. 8 is a front plan view of an alternative embodiment of the eye occluder of the present invention.

FIG. 9 is a side elevation view of the eye occluder assembly of the present invention.

DETAILED DESCRIPTION OF THE INVENTION

A self-adherent eye occluder constructed in accordance with the present invention can be seen in FIGS. 1-9. Eye occluder 10 can be constructed to be disposable and constructed to drape or contour over an eye, thereby substantially blocking vision of an eye, without necessarily being fully light occlusive when it is placed on periorbital tissue 12, as shown in FIG. 1. FIG. 1A shows eye occluder 10 placed directly on spectacles 14. Eye occluder 10 can include a pressure-sensitive adhesive material 16 applied to at least a portion of posterior side 18 of eye occluder 10, as shown in FIGS. 2-4. Adhesive material 16 should be sufficiently tacky to adhere eye occluder 10 to either periorbital tissue 12 or to spectacles 14 worn over the eye.

Eye occluder 10 can be constructed to be any shape which drapes or contours over the eye and which substantially blocks or modifies vision of the eye. For example, eye occluder 10 can have an elliptical shape as shown in FIGS. 1-4 or, alternatively, a square shape as shown in FIG. 5.

Eye occluder 10 can be formed of any suitable material which is economical and non-irritating to the skin, and which will not scratch spectacle lenses 14. Therefore, eye occluder 10 can be formed of either a supple material or a firm material. Eye occluder 10 is preferably hypo-allergenic and can be constructed, for example, of materials such as paper, cardboard, plastic, or cloth.

Adhesive material 16 is preferably applied to a posterior surface 18 of at least a portion of peripheral edges 20 of eye occluder 10. Adhesive 16 can be pressure-sensitive so that when pressure is applied to anterior surface 34, eye occluder 10 will adhere to either periorbital tissue 12 or spectacles 14. Thus, adhesive 16 can be applied to an upper edge of eye occluder 10, or to its side edges, a lower edge, or a center portion of the posterior surface, or a combination thereof. The determination of adhesive placement will depend on the use which is being made of eye occluder 10.

Adhesive material 16 of eye occluder 10 should preferably be biocompatible with the wearer's skin and should have sufficient tackiness to adhere to the skin, eyebrows or other periorbital tissue 12, spectacles 14 or without leaving significant residual debris on the surface it is adhered to. Preferably, adhesive 16 should have high shear qualities so that eye occluder 10 adheres to skin or spectacles 14 against the force of gravity.

In an alternate embodiment of the present invention, eye occluder 10 can include tab 22 at its lower edge 24 to facilitate handling, placement, and removal of eye occluder 10. An illustration of this embodiment can be seen in FIGS. 3 and 4. Adhesive material 16 can be applied to posterior surface 26 of tab 22 for increased adhesiveness.

Another embodiment of the present invention can include eye occluder 10 perforated with a plurality of pinholes 28 or, thin slit opening 19 positioned at the approximate center of eye occluder 10, as shown in FIGS. 4 and 5, respectively. These embodiments are useful for screening in determining a patient's best possible visual accuity without performing a full refractive examination.

Another embodiment of the present invention is shown in FIGS. 6-7 wherein mask-type frame 30 can be constructed with openings 32 in front of the eyes, for accepting eye occluder 10 of the present invention. In this embodiment, one or both eyes can be occluded with eye occluder 10 constructed in accordance with the present invention and adhered to mask 30. Mask 30 can be constructed of a permanent material such as plastic or metal, or alternatively, can be constructed of a disposable material such as cardboard or plastic. Eye occluder 10 of the present invention can be positioned over openings 32 of mask 30 by applying pressure to an anterior surface 34 opposite posterior surface 18 at which adhesive 16 has been applied. Eye occluder 10 will adhere to frame 30 and one or both eyes can be occluded. Frame 30 permits easy positioning of eye occluder 10 with a minimum of discomfort to the wearer.

Eye occluder 10 can be constructed to include advertising or other information printed on anterior surface 34 as shown in FIG. 1. For example, an eye chart can be printed on anterior surface 34 of eye occluder 10 so that the physician can ask the patient to read a specific line and be able to know the exact letters or figures to be read by the patient on a specific line on the visual chart. Anterior surface 34 of eye occluder 10 can also be imprinted with a variety of information which a sponsor may want to convey to the eye practitioner or technician. Alternatively, notes can be written on anterior surface 34 of occluder 10 about the patient's condition or treatment, or to place information on the patient's chart, or give instructions to the patient.

Another embodiment of the present invention can include self-adherent semi-opaque or opaque eye occluder 10 designed to drape or contour over an eye and having opening 36 for accepting trial lenses 38 for refractive examination, or other diagnostic lenses 40, such as prism lenses, Maddox rods, red lenses, or green lenses as shown in FIG. 8. In this embodiment, envelope-like support member 40a can be positioned at the lower edge of opening 36 for inserting a bottom edge of lens 40, for secure positioning within eye occluder 10.

The present invention can also include eye occluder assembly 42 as shown in FIG. 9 for use in visual diagnostic testing and treatment. Eye occluder assembly 42 is preferably constructed as a pad-like assembly 42 for use in visual diagnostic testing and treatment. Eye occluder assembly 42 can include a plurality of disposable eye occluders 44 constructed in accordance with the present invention. Each separate eye occluder 10 can be designed to drape or contour over an eye and to substantially block vision without being fully light occlusive when placed over the eye. Each eye occluder 10 can further include pressure-sensitive adhesive material 16 applied to at least a portion of posterior surface 18, and preferably, a portion of peripheral edges 20. Adhesive 16 preferably should be applied to a portion of peripheral edges 20 sufficient to adhere each eye occluder 10 to either periorbital tissue 12 or spectacles 14. Plurality of eye occluders 44 can be stacked successively on each other in pad-like assembly 42 and eye occluders 10 can be removably bound to each other by adhesive 16. When pressure is applied to anterior surface 34 of one eye occluder 10 of assembly 42, adhesive 16 can removably fasten eye occluder 10 to anterior surface 34 of second eye occluder 10. Thus, assembly 42 can be constructed so that a user can remove a single eye occluder 10 from assembly 42 for covering a patient's eye as needed. Eye occluder assembly 42 is portable, allowing a patient or physician to carry assembly 42 in a pocket, wallet, or purse so that it is easily accessible for use.

The present invention also includes a method for occluding an eye for visual testing and treatment using eye occluder 10 constructed in accordance with the present invention. The method of the present invention can include placing self-adherent eye occluder 10 on periorbital tissue 12 or spectacles 14, wherein eye occluder 10 is designed to drape or contour over an eye without being fully light occlusive. Eye occluder 10 can further include pressure-sensitive adhesive material 16 applied to at least a portion of posterior side 18, preferably a portion of peripheral edges 20 of eye occluder 10 sufficient to adhere eye occluders 10 to either periorbital tissue 12 or to spectacles 14. The method can further include applying pressure to anterior side 34 of eye occluder 10 opposite a portion of posterior side 18 at which adhesive 16 is applied, to cause eye occluder 10 to adhere to either periorbital tissue 12 or spectacles 14.

The method of the present invention can further comprise transcribing medical records or other information, including advertising, on anterior surface 34 of occluder 10 for efficient recordkeeping, treatment, and conveyance of product information.

What is claimed is :

1. A disposable self-adherent eye occluder for use in visual diagnostic testing and treatment said eye occluder comprising eye occluder means including a flexible thin sheet, having top and bottom edges and posterior and anterior sides, and a pressure-sensitive adhesive material applied directly only to a region proximal to the top edge of the posterior side of said flexible sheet, said adhesive being capable of adhering said eye occluder to either the periorbital tissue of said eye or to spectacles worn over said eye, said flexible sheet shaped to contour to periorbital tissue, said eye occluder means being constructed to cause said flexible thin sheet to flexibly drape or contour over only one eye and to depend downwardly and terminate in a free end to substantially block the forward vision of said eye, without being fully light occlusive to the eye's periphery when said eye occluder is placed over said eye.

2. The eye occluder of claim 1 wherein said flexible sheet is constructed of a material selected from the group of paper, plastic, cardboard and cloth.

3. The eye occluder of claim 1 wherein said adhesive material is biocompatible and is hypo-allergenic.

4. The eye occlude of claim 1 further comprising a tab at a lower surface of said eye occluder.

5. A method of occluding an eye for visual diagnostic testing and treatment comprising the step of:
  (a) placing a disposable self-adherent eye occluder on periorbital tissue or spectacles of a patient for visual diagnostic testing and treatment, said eye occluder comprising eye occluder means including a flexible thin sheet, said flexible thin sheet having top and bottom edges and posterior and anterior sides, said flexible thin sheet being shaped to contour to periorbital tissue and a pressure-sensitive adhesive material applied only to a region proximal to the top edge of a posterior side of said eye occluder and adhering said eye occluder directly to either said periorbital tissue or to said spectacles causing said flexible thin sheet to flexibly drape or contour over the eye and to depend downwardly and terminate in a free end to block the patient's forward vision without being fully light occlusive to the eye's periphery.

6. The method of claim 5 further comprising the step of:
   (b) transcribing medical information or instructions onto an anterior surface of said occluder for efficient record-keeping and treatment.

7. The method of claim 5 wherein said placing step further comprises applying pressure to an anterior side of said eye occluder opposite a portion of said posterior side at which said adhesive material is applied, to cause said eye occluder to adhere to one of said periorbital tissue or said spectacles.

8. The method of claim 5 wherein said eye occluder is disposable.

9. The method of claim 5 wherein said eye occluder is constructed of a material selected from the group of paper, plastic, cardboard and cloth.

10. The method of claim 5 wherein said adhesive material is biocompatible with the skin of a wearer of said eye occluder and is hypo-allergenic.

11. The method of claim 5 wherein said eye occluder further comprises a tab at a lower surface of said eye occluder to facilitate handling and placement of said eye occluder.

12. The method of claim 5 wherein said eye occluder is perforated with a plurality of pinholes at an approximate center of said eye occluder for visual testing.

13. The method of claim 5 wherein said eye occluder contains a slit opening at an approximate center of said occluder for visual testing.

* * * * *